United States Patent [19]
Gettig

[11] Patent Number: 4,581,016
[45] Date of Patent: Apr. 8, 1986

[54] DUAL CARTRIDGE WET/DRY SYRINGE

[75] Inventor: William A. Gettig, Millheim, Pa.

[73] Assignee: Gettig Pharmaceutical Instrument Co., Spring Mills, Pa.

[21] Appl. No.: 584,883

[22] Filed: Feb. 29, 1984

[51] Int. Cl.⁴ .............................................. A61M 3/00
[52] U.S. Cl. .......................................... 604/88; 604/92
[58] Field of Search ........................ 604/56, 82, 88, 92

[56] References Cited
U.S. PATENT DOCUMENTS

| | | | |
|---|---|---|---|
| 2,841,145 | 7/1958 | Epps | 604/89 |
| 3,327,710 | 6/1967 | Freeberg et al. | 604/88 |
| 3,542,023 | 11/1970 | Ogle | 604/88 |
| 3,636,950 | 1/1972 | Gomez et al. | 604/88 |
| 3,724,460 | 4/1973 | Gomez et al. | 604/88 |
| 3,785,379 | 1/1974 | Cohen | 604/88 |
| 3,911,916 | 10/1974 | Stevens | 604/191 |
| 3,916,894 | 11/1975 | Cloyd | 604/203 |
| 3,946,732 | 3/1976 | Hurschman | 604/88 |
| 3,995,630 | 12/1976 | Van de Veerdonk | 604/88 |
| 4,031,892 | 6/1977 | Hurschman | 604/88 |
| 4,031,895 | 6/1977 | Porter | 604/88 |
| 4,059,109 | 11/1977 | Tischlinger | 604/88 |
| 4,171,698 | 10/1979 | Genese | 604/88 |
| 4,221,218 | 9/1980 | Pfleger | 604/218 |
| 4,235,235 | 11/1980 | Bekkering | 604/238 |
| 4,392,850 | 7/1983 | Elias et al. | 604/416 |
| 4,407,283 | 10/1983 | Reynolds | 604/233 |
| 4,424,057 | 1/1984 | House | 604/88 |

Primary Examiner—Andrew H. Metz
Assistant Examiner—Anthony McFarlane
Attorney, Agent, or Firm—Emory L. Groff, Jr.

[57] ABSTRACT

A multi-cartridge syringe assembly includes one cartridge containing a diluent and insertable within another cartridge containing dry medication. The nose of the diluent cartridge supports a cannula and is surrounded by a lock head member. In an initial mode, the exposed cannula is surrounded by a resilient cover. A retaining element extending rearwardly from a piston in the medication cartridge includes lock elements sequentially engageable with first and second annular devices on the lock head member as the two cartridges are axially displaced towards each other. In a first position the two cartridges are locked together without any axial displacement between the cannula and its cover while in a second position the cover is forced rearwardly of the cannula as the point of the cannula pierces the cover as well as the piston in the medication cartridge.

11 Claims, 4 Drawing Figures

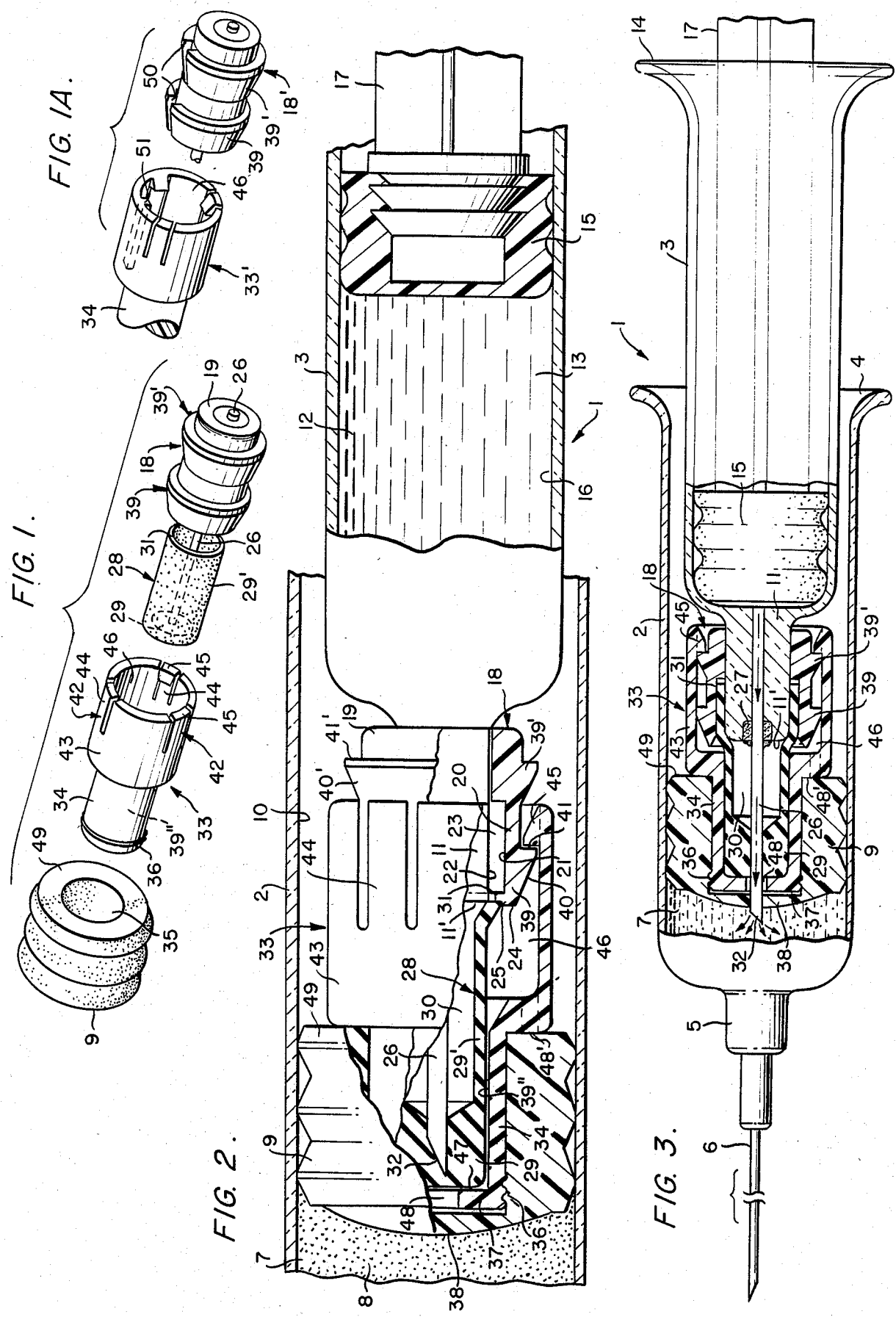

DUAL CARTRIDGE WET/DRY SYRINGE

This invention relates generally to syringes and more particularly to an improved syringe containing two disparate components initially disposed in two adjacent cartridges and wherein the components are admixed immediately prior to administration.

The broad concept of dual cartridge syringes is generally well known and has been employed for years as a convenient means for mixing two premeasured components immediately prior to the injection of the medicament mixture into a patient. The advantages of such an arrangement will be obvious to those skilled in the art. A primary benefit is that many premixed medications have a relatively short shelf life whereas the wet and dry components thereof, if stored separately, not only have a substantially longer shelf life but also often may be stored without the same constraints as to temperature, etc. In this regard, the present invention will be understood to be used primarily with a powder or dry component and a separate wet or fluid component, the latter serving as a diluent admixing with the former to produce a prescribed medicament adapted to be injected into a patient immediately following said admixture. Alternately, two disparate fluid components can be utilized without departing from the spirit of the present invention.

Many prior known dual cartridge syringes require extreme care when handling since they are shipped from the pharmaceutical house in a condition raking them quite vulnerable to accidental, premature mixture of the diluent and medicament. Many of these syringes utilize a second cannula juxtaposed the diluent cartridge which is designed to rupture a septum serving as the sole barrier between the diluent and medicament powder and accordingly, inadvertent pressure upon the end of the diluent cartridge plunger may cause at least rupture of this barrier septum.

With the present invention, an improved arrangement is offered wherein the diluent cartridge and medicament cartridge comprise separate sub-assemblies which may alternately be separately shipped or only partially assembled prior to shipment and in either case, a positive further assembly step is required prior to admixture of the components, which assembly step causes the diluent cartridge cannula to rupture both a rubber cannula cover as well as a septum forming a part of the plunger piston of the medicament cartridge. The referenced manipulation involves the axial displacement of the diluent cartridge which carries a lock head member having a plurality of ridges thereon which ridges sequentially cooperate with a plurality of snap lock elements carried by a retainer supported by the plunger piston in the medicament cartridge. With the foregoing arrangement, the two sub-assemblies may be readily stored in a sterile condition prior to assembly therebetween and when subsequently assembled together, a positive multiposition relationship is exhibited as the diluent cartridge is axially displaced relative the medicament cartridge with the first position fixedly joining the two sub-assemblies without any admixture of the components thereof so that upon further axial displacement of the diluent cartridge, the cannula thereof ruptures two membranes or seals between the cartridges to allow admixture of the components and subsequent administration of the ready medicament to a patient.

Accordingly, one of the objects of the present invention is to provide an improved dual cartridge wet/dry syringe including separate diluent and medicament cartridges with a lock head member on the diluent cartridge provided with a plurality of axially spaced ridges cooperating with a snap retainer carried by the piston located in the medicament cartridge.

Another object of the present invention is to provide an improved dual cartridge wet/dry syringe including a pair of nesting cartridges respectfully supporting relatively axially displaceable locking and retaining members allowing alternate assembled positions between the two cartridges with the first position attaching one cartridge to the other and the second position causing a cannula carried by one cartridge to pierce barrier means previously isolating the contents of the two cartridges.

A further object of the present invention is to provide an improved dual cartridge wet/dry syringe including a diluent cartridge having a lock head member provided with a cannula normally enveloped by a rupturable cover and a sleeve-like retainer within the other of the cartridges axially receiving the cannula cover and forcing the cover rearwardly into a recess of the lock head during axial advancement of the diluent cartridge.

With these and other objects in view which will more readily appear as the nature of the invention is better understood, the invention consists in the novel construction, combination and arrangement of parts hereinafter more fully described, illustrated and claimed.

BRIEF DESCRIPTION OF THE DRAWINGS

FIG. 1 is an exploded perspective view illustrating the lock head and snap retainer member of the present invention;

FIG. 1A is an exploded perspective view of an alternate arrangement of the structure of FIG. 1;

FIG. 2 is an enlarged fragmentary longitudinal view, partly in section, of the syringe of the present invention with the components in a first assembled position; and FIG. 3 is a view similar to FIG. 2 with the components shown as they appear after shifting to a second position and during injection of the medicament into a patient.

Similar reference characters designate corresponding parts throughout the several figures of the drawing.

The dual cartridge syringe as shown in FIGS. 2 and 3 of the drawing is generally designated 1 and will be seen to include a first cartridge 2 and a second cartridge 3, the latter being of a smaller diameter than the former and adapted to be nested or inserted through the end opening 4 of the first cartridge 2. The first cartridge 2 includes a forward nose 5 from which projects a cannula 6 adapted to be inserted into a patient and the interior or chamber 7 of this cartridge will be understood initially to be supplied with a premeasured amount of medication preferably in the form of powder 8 such as shown in FIG. 2. This powder medication 8 is retained within the chamber 7 of the first cartridge 2 by means of a medicament plunger piston 9 forming a close sliding fit with respect to the surrounding inner wall 10.

The smaller diameter second cartridge 3 serves as the diluent cartridge and is likewise provided with a nose 11 communicating with the cartridge interior or chamber 12. This chamber 12 is adapted to be supplied with a premeansured amount of an appropriate fluid or diluent 13 adapted to admix with the powder 8 in the cartridge 2 to instantly produce the desired medicament in the chamber 7 of the first cartridge ready for administration to a patient by means of the cannula 6.

The diluent 13 is contained within the second cartridge chamber 12 by means of an appropriate plunger piston 15 forming a fluid tight sliding fit with the inner wall 16 thereof. An actuator shaft or rod 17 appropriately attached to the plunger and is axially displaceable with respect to the cartridge 3 in a well known manner to force the diluent 13 from the cartridge 3 through its nose 11 as will be described hereinafter. As previously mentioned, the diluent containing cartridge 3 may be initially supplied as a separate sub-assembly adapted to be later assembled with the remainer of the syringe 1 at any time prior to admixture of the components of the two cartridges.

The foregoing is facilitated by means of a lock head member 18 affixed to the exterior of the second cartridge nose 11 and which comprises a hollow elongated cylindrical member having a mounting base 19 appropriately affixed to the cartridge nose 11 adjacent the rear thereof by any suitable means such as adhesive. The forward portion of the lock head 18 comprises a spaced sleeve 20 which from FIG. 2 will be seen to include an inner wall 21 outwardly spaced from the periphery 22 of the cartridge nose 11 a sufficient distance to provide an annular recess 23 completely encircling the nose 11. The forward edge 24 of the lock head sleeve 20 extends to a forward plane substantially coincident with the forward edge 11' of the nose 11 and includes an inwardly and rearwardly directed bevel 25, the purpose of which will become apparent hereinafter. Axially disposed through the nose 11 is a diluent cartridge cannula 26 which is suitably affixed with respect thereto such as by the adhesive 27.

During the initial assembly of the diluent containing cartridge 3, the entire portion of the cannula 26 projecting from the cartridge nose 11 is surrounded and protected by a resilient cover 28 comprising a cylindrical member preferably formed of rubber having a closed end wall 29 at its forward end of substantially greater thickness than the side wall 29' and an inner cavity 30 extending rearwardly to the cover rear edge 31. This cover 28 is illustrated in FIG. 1 in a slightly axially exploded position relative the lock head member 18 for purposes of clarity. Axially assembled with respect to the diluent cartridge 3 and before operation of the syringe, the cover will appear as in FIG. 2 wherein it will be seen that the cannula forward point 32 is fully enveloped as it is embedded within the body of the cover end wall 29 while the rear edge 31 of the cover resiliently engages the forward portion of the nose 11 of the cartridge 3 juxtaposed the forward portion of the annular recess 23 and adjacent the nose forward edge 11'. The internal diameter of the resilient cover 28 is preferably of a slightly lesser diameter than that of the cartridge nose 11 so that when fitted in place, the rear edge 31 thereof is biased outwardly by the slightly rounded corner of the nose 11. In this manner, the cannula 26 will be seen to be fully protected and sealed against any contamination thereof during handling of the diluent cartridge 3 as a separate sub-assembly or when later disposed in the first assembled position of FIG. 2.

The just-described diluent cartridge sub-assembly is adapted to be joined to the powder cartridge 2 by the inneraction of the lock head member 18 and a retainer element 33 attached to the medicament plunger piston 9. This retainer element includes a reduced diameter sleeve portion 34 at its forward end disposed within a central recess 35 formed in the plunger piston 9. Suitable means such as cooperative ridges 36 insures fixation between the retainer element 33 and the plunger piston 9 with the forward wall 37 of the sleeve 34 juxtaposed the relatively thin septum 38 of the plunger piston 9. The bore 39" of the sleeve 34 is formed with a diameter slidably receiving the external periphery of the cannula cover 28 as the two cartridges 2,3 are initially assembled as shown in the first position of FIG. 2 of the drawing.

A positive attachment between the two cartridges is provided by features carried by both the lock head member 18 on the diluent cartridge 3 and the retainer element 33 affixed within the medicament cartridge 2. These features include two annular ridges or enlargements 39—39' axially spaced apart and radially projecting from the lock head member 18 as shown in all figures of the drawing. Each ridge preferably comprises a rearwardly directed inclined wall 40 or 40' communicating with a rearwardly facing, radial shoulder 41 or 41' and these ridges are designed to sequentially cooperate with a plurality of locking elements 42 carried by the enlarged barrel portion 43 of the retainer element 33. Three such locking elements 42 are shown in the drawing and quite obviously any number of these elements may be provided. Each locking element 42 will be seen to include an integral construction comprising a resilient finger 44 terminating in an inwardly directed hook snap 45 normally disposed in a radial plane adapted to engage the inclined walls 41—41' of the annular ridges 39—39' of the lock head member 18 carried by the diluent cartridge 3.

With the foregoing structure in mind, it will be appreciated that upon the initial assembly of the diluent cartridge 3 with the medicament cartridge 2, the resilient cannular cover 28 will be inserted through the bore 46 of the retainer element 33 and thereafter into the reduced diameter bore 39" thereof and just prior to the resilient cover end wall 29 reaching the end or bottom 47 of the bore 39" the forwardmost annular ridge 39 engages the plurality of lock elements 42 and outwardly deflects the same until the hook snaps 45 thereof snap back inwardly behind the rearwardly facing shoulder 41 of the ridge 39. In this first assembled position, the various components will appear as shown in FIG. 2 of the drawing which represents the assembly of the components just prior to initiation of the admixture of the diluent 13 and the powder medication 8.

Mixture of the components is achieved by advancing the cartridge 3 forwardly with respect to the cartridge 2 to axially displace the lock head member 18 with respect to the cooperating retainer element 33 from the first position of FIG. 2. This displacement will be understood to initiate a series of concurrent events. As the cartridge body 3 is advanced, the lock head member and retainer element shift from the position shown in FIG. 2 to that as represented in FIG. 3 wherein the plurality of lock elements 42 on the retainer element 33 are deflected outwardly by the second annular ridge 39' and thereafter snap fit inwardly to engage the rearwardly facing shoulder 41'. At the same time, the forward point 32 of the diluent cartridge cannula 26 slices through the balance of the thickness of the end wall 29 of the resilient cover 28, passes through an end opening 48 in the forward wall 37 of the retainer element 33 and ruptures the septum 38 of the medicament plunger 9. The retainer element 33 and lock head member 18 will then appear as depicted in FIG. 3 wherein it will be seen that the forward point 32 of the diluent cannula 26 is now disposed within the chamber 7 of the medicament cartridge 2 such that subsequent axial displacement of the actuator rod 17 with respect to its cartridge 3 will propel the diluent 13 into the medicament chamber 7 to allow admixture of the two components in this forwardmost chamber. The prepared medicament is then administered bv means of the cannula 6 in a known prescribed mannr by grasping the forward cartridge 2 while applying forward pressure upon the actuator 17 so as to advance the medicament piston 9.

During the axial collapse between the lock head member 18 and retainer element 33, the rear edge 31 of the resilient cover 28 is directed, by means of the bevel 25, into the annular recess 23 which is of an axial extent sufficient to accommodate so much of the resilient cover as is displaced during the relative movement between the lock head member and retainer element. The above described arrangement of two separate annular ridges or enlargements 39,39' will be seen to provide a non-reversible assembly of the two cartridges of the invention in two positive positions.

With the construction of the lock head member 18 as shown most cleary in FIG. 1, it is conceivable that when the components are assembled in either of the two locked positions and likewise during the axial displacement during assembly of the components, that rotary displacement of one cartridge with respect to the other cartridge could produce a coreing of either or both the end wall 29 of the resilient cover 28 and the septurm 38 of the medicament plunger piston 9, due to the sharpened bevel end point 32 of the cannula 26. FIG. 1A of the drawing depicts but one alternate arrangement which precludes relative rotary displacement between the lock head member and retainer element. As shown in this alternate construction, an axially extending slot 50 is formed in the bodv of the lock head member 18' and passes through both annular ridges 39,39' thereof. This slot cooperates with an inwardly directed ridge 51 extending into the bore 46 of the retainer element barrel 43 so that as soon as the forward portion of the lock head member 18' is inserted into the bore 46 of the retainer element 33', the diluent cartridge 3 must be annularly oriented to allow the ridoe 51 to enter the slot 50 and thereafter the subsequent axial collapse or forward displacement of the diluent cartridoe 3 occurs without any relative annular displacement between the diluent cartridge and the retainer element 33. In this manner, when the components are advanced or collapsed to the second locked position of FIG. 3, the forward point 33 of the cannula 26 pierces both the end wall 29 of the resilient cover 28 and the septum 38 in a straight line manner discouraging coreing of the respective resilient components. A further modification not shown in the drawing would be to angularly offset the slot 50 passing through the two ridges 39,39' and to connect the two offset portions between these two ridges by means of a right angular slot such that during use, it would be necessary to rotate the diluent cartridge 3 with respect to medicament cartridge 2, for example a quarter turn, in order to axially displace the components between the first and second locked positions.

Since the medicament plunger piston is relatively thin along its forward face in view of the septum 38, additional means are provided to preclude rupture of the piston when forward pressure is applied thereto by the retainer element. The barrel 43 and sleeve 34 of the retainer element will be seen to be joined by a radially extending, forwardly facino shoulder 48' which abuts the rear wall 49 of the piston 9 so that forward forces applied to the piston 9 by the cartridge 3 and retainer element 33 will be directed against the thickest axial portion of the piston.

I claim:

1. A hypodermic syringe assembly comprising initially separated first and second cartridges each having opposite nose and open end portions, said first cartridge chamber initially containing one component of a medicament and said second cartridge chamber initially containing another component of a medicament, said second cartridge nose insertable through said first cartridge open end portion at any time prior to use of said assembly upon a patient, a slidable plunger piston within each said cartridge defining a variable volume chamber within each said cartridge between each said piston and its respective cartridge nose, a plunger actuator rod fixedly joined to and extending rearwardly of said piston in said second cartridge, a lock head member fixed to and surrounding said second cartridge nose, axially spaced two-position catch means on said lock head member, a cannula fixed to and extending through said second cartridge nose and having a forward point extended beyond said lock head member, a resilient cover initially enveloping said forward cannula point and a substantial portion of said cannula forward of said lock head member, a retainer element fixed to and projecting rearwardly of said piston in said first cartridge and having a central bore therein, lock means on said retainer element, said cover-enveloped second cartridge cannula axially insertable within said first cartridge in a forward direction with said cover entering said retainer element bore whereupon said lock means engages said catch means in a first position to lock said second cartridge relative said first cartridge piston without said cannula forward point extending forwardly of said retainer element, said second cartridge and lock head member further axially insertable within said retainer element bore to a second position locking said second cartridge to said first cartridge piston whereby said cannula forward point pierces said cover and said first cartridge piston and enters said first cartridge chamber as said lock head member catch means is forwardly and axially advanced reltive said retainer element lock means, said second cartridge, lock head member, second cartridge cannula, cover, retainer element and first cartridge piston defining a relatively fixed sub-assembly following attainment of said second position, and another cannula extending forwardly from said first cartridge nose whereby, following disposition of said lock head member to said second position, axial displacement of said actuator rod fully forward within said second cartridge forces said another component into said first cartridge chamber with subsequent mixture with said one component within said first cartridge chamber whereafter subsequent forward axial displacement of said second cartridge with its actuator rod concurrently advances said first cartridge piston to eject the mixed components through said first cartridge cannula.

2. A hypodermic syringe assembly according to claim 1 wherein, said catch means includes a pair of axially-spaced radially-extending projections on said lock head member.

3. A hypodermic assembly according to claim 1 wherein, said cannula cover is substantially cylindrical and includes an endwall and sidewall having a rear edge, and in said first position said endwall overlying said cannula point and said sidewall rear edge juxtaposed said lock head member and second cartridge nose.

4. A hypodermic assembly according to claim 1 wherein, said lock means on said retainer element comprise a plurality of resilient snap fingers.

5. A hypodermic assembly according to claim 1 wherein, said retainer element includes a rearmost barrel joined to a reduced diameter sleeve having a perforated end wall whereby with said lock head member and retainer element in said first position the forward portion of said cover is nested within said sleeve juxtaposed said endwall.

6. A hypodermic assembly according to claim 1 wherein, said one component comprises a powder and said another component comprises a diluent.

7. A hypodermic assembly according to claim 2 wherein, said pair of projections include annular ridges each having a rearwardly and outwardly directed wall joined to a rearwardly facing shoulder and said shoulders adapted to sequentially receive and retain said retainer element lock means as said lock head member is axially displaced to said first and second positions.

8. A hypodermic assembly according to claim 2 wherein, said lock means on said retainer element comprise a plurality of resilient snap fingers.

9. A hypodermic assembly according to claim 3 wherein, said lock head member includes a forward sleeve surrounding said second cartridge nose, said sleeve radially spaced from said second cartridge nose to define an annular recess therebetween whereby, as said lock head member is displaced to said second position said cover rear edge is driven by said retainer element into said recess.

10. A hypodermic assembly according to claim 4 wherein, said fingers comprise integral portions of said retainer element.

11. A hypodermic assembly according to claim 7 wherein, said pair of ridges each include an axially extending slot therethrough and an inwardly directed ridge on said retainer element insertable through said slots to preclude relative angular displacement between said lock head member and retainer element during displacement between said first and second positions.

* * * * *